United States Patent
Fishlock et al.

(10) Patent No.: US 9,828,340 B2
(45) Date of Patent: Nov. 28, 2017

(54) ASYMMETRIC SYNTHESIS OF A SUBSTITUTED PYRROLIDINE-2-CARBOXAMIDE

(71) Applicant: Hoffmann-La Roche Inc., Nutley, NJ (US)

(72) Inventors: Daniel Fishlock, Basel (CH); Chen Gu, Lake Hiawatha, NJ (US); Lianhe Shu, Livingston, NJ (US); Pankaj Devdatta Rege, Basel (CH); Keshab Sarma, Sunnyvale, CA (US)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 14/766,049

(22) PCT Filed: Feb. 18, 2014

(86) PCT No.: PCT/EP2014/053057
§ 371 (c)(1),
(2) Date: Aug. 5, 2015

(87) PCT Pub. No.: WO2014/128094
PCT Pub. Date: Aug. 28, 2014

(65) Prior Publication Data
US 2016/0002158 A1    Jan. 7, 2016

Related U.S. Application Data

(60) Provisional application No. 61/767,395, filed on Feb. 21, 2013, provisional application No. 61/909,520, filed on Nov. 27, 2013.

(51) Int. Cl.
C07D 207/16    (2006.01)
(52) U.S. Cl.
CPC ............................... C07D 207/16 (2013.01)
(58) Field of Classification Search
CPC .................................................... C07D 207/16
See application file for complete search history.

(56) References Cited

U.S. PATENT DOCUMENTS

2012/0010235 A1    1/2012   Chu et al.

FOREIGN PATENT DOCUMENTS

WO    2011/098398    8/2011

OTHER PUBLICATIONS

The Japanese Office Action, dated Sep. 20, 2016, in the corresponding Japanese Application No. 2015-558415.
Shu et al., "Synthesis of a Spiroindolinone Pyrrolidinecarboxamide MDM2 Antagonist," Organic Process Research & Development, vol. 17(2), pp. 247-256 (2013).

*Primary Examiner* — Valerie Rodriguez-Garcia

(57) ABSTRACT

The invention relates to a process for the preparation of 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid of the formula (I)

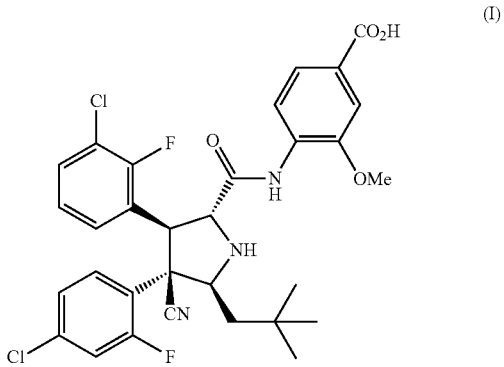

as well as intermediates thereof and pharmaceutical preparations thereof, comprising the step of reacting a compound of the formula (IV) with a compound of the formula (V), as defined in the specification, in the presence of a chiral silver- or copper catalyst.

8 Claims, 1 Drawing Sheet

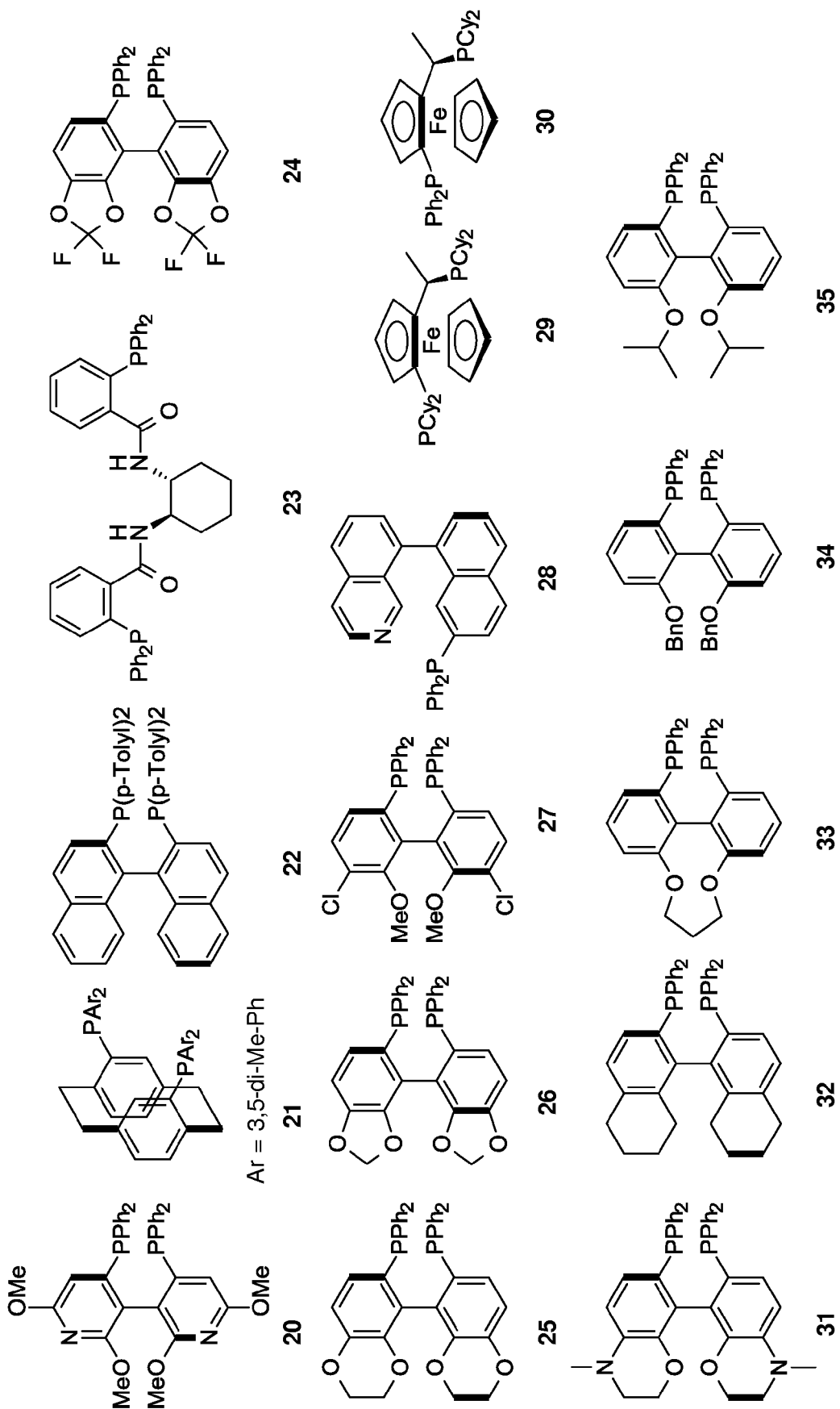

US 9,828,340 B2

ASYMMETRIC SYNTHESIS OF A SUBSTITUTED PYRROLIDINE-2-CARBOXAMIDE

CROSS-REFERENCE TO RELATED APPLICATIONS

This application is a National Stage Application of PCT/EP2014/053057 filed Feb. 18, 2014, which claims priority from U.S. Provisional Patent Application No. 61/767,395, filed on Feb. 21, 2013 and U.S. Provisional Patent Application No. 61/909,520, filed on Nov. 27, 2013. The priority of said PCT and U.S. Provisional Patent Applications are claimed. Each of the prior mentioned applications is hereby incorporated by reference herein in its entirety.

FIELD OF THE INVENTION

The invention relates to a process for the preparation of 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid of the formula (I)

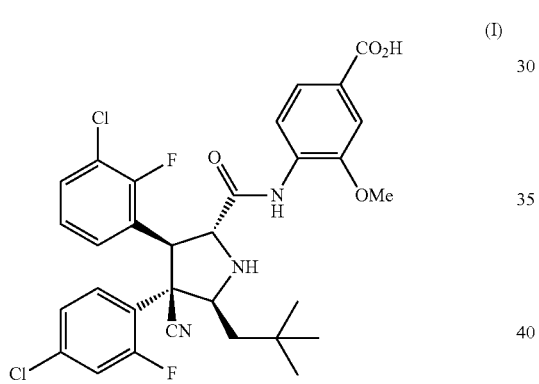

as well as novel intermediates.

BACKGROUND OF THE INVENTION

The compound of formula I (herein sometimes designated as compound (I) or 5) is a non-peptidic, highly selective small-molecule antagonist of the protein-protein interaction between MDM2 and tumor suppressor protein p53. Inhibition of MDM2, the principal cellular antagonist of p53, leads to p53 pathway activation and apoptosis of cells carrying potential oncogenic mutations. This therapeutic approach (MDM2 inhibition) is currently under development as a novel strategy for cancer treatment. A previous synthesis of Compound I was reported in U.S. patent application Ser. No. 12/702,402, where Compound IIa is obtained from the racemate II by a chiral column chromatography method and coupled with Compound III followed by hydrolysis of the ester to give Compound I as shown in Scheme 1. The overall yield of compound (I) JB, 17/Jan./2014 relative to starting material of compound (IV) as used herein (see e.g. scheme 5) using this process is about 10%. There remains a need to develop improved methods for large, industrial scale production of compound (I).

Scheme 1

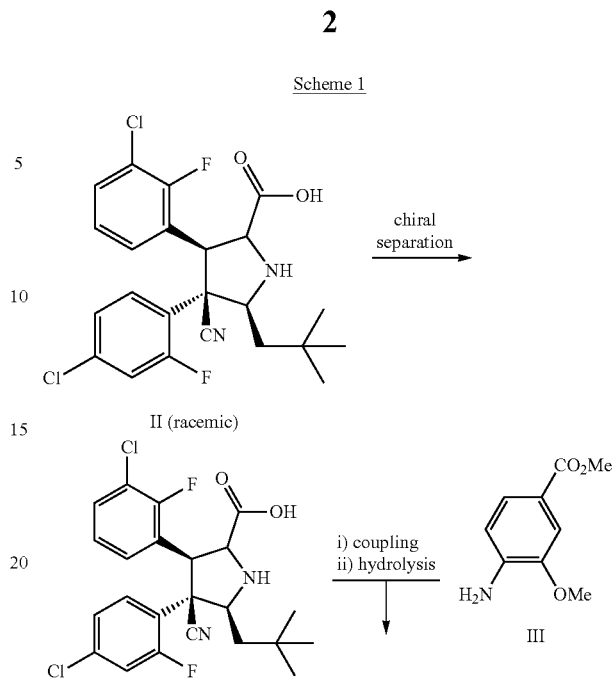

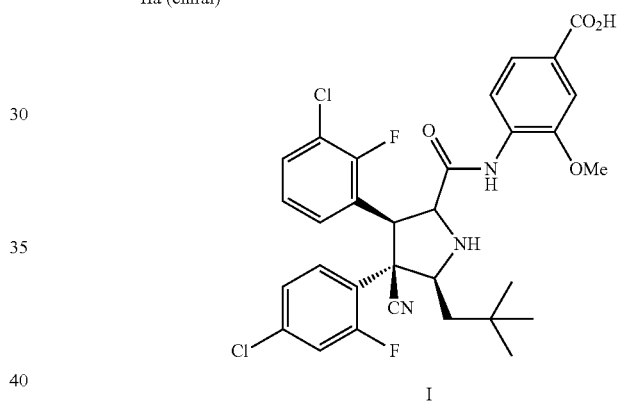

SUMMARY OF THE INVENTION

In one embodiment, the present invention provides an improved method for the large scale production of the compound 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid having the structural formula

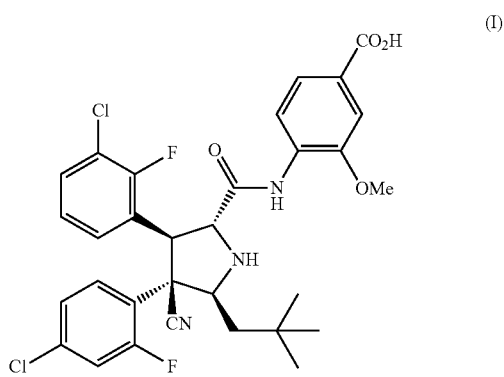 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

as well as novel intermediates.

The optimized process is operationally more simple, has higher throughput, higher overall yield and is more robust and reproducible.

In another embodiment, steric isomers of ethyl esters of compound (I) having the formulas (6) and (7) are provided.

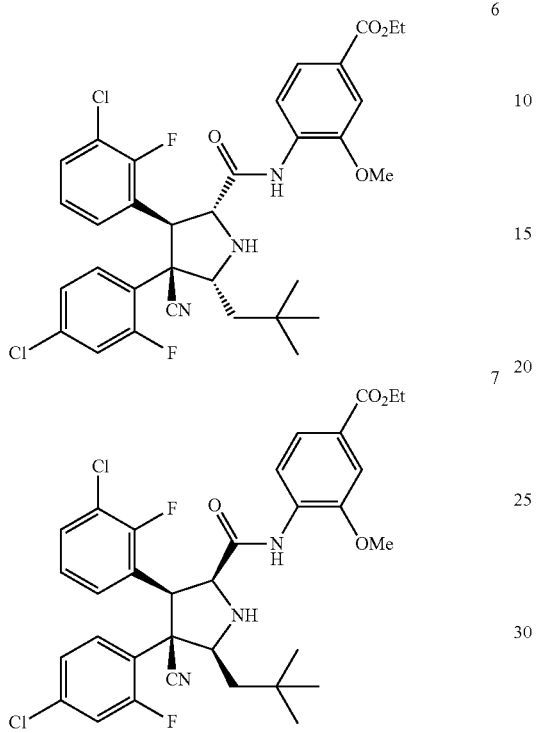

These compounds are intermediates in the present process.

BRIEF DESCRIPTION OF THE FIGURES

FIG. 1: Chemical formulae of ligands used for the ligand screening according to Table 1.

DETAILED DESCRIPTION OF THE INVENTION

As used herein, the following terms shall have the following definitions.

The term "alkyl" refers to straight- or branched-chain saturated hydrocarbon groups having from 1 to about 12 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, preferably from 1 to 4 carbon atoms. Examples of alkyl groups include, but are not limited to, methyl, ethyl, n-propyl, i-propyl, n-butyl, s-butyl, t-butyl, n-pentyl, and s-pentyl.

The term "alkenyl" as used herein means an unsaturated straight-chain or branched aliphatic hydrocarbon group containing at least one double bond and having 2 to 6, preferably 2 to 4 carbon atoms. Examples of such "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"Alkoxy, alkoxyl or lower alkoxy" refers to any of the above lower alkyl groups which is attached to the remainder of the molecule by an oxygen atom (RO—). Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like. Amino means the group —NH2.

"Aryl" means a monovalent, monocyclic or bicyclic, aromatic carboxylic hydrocarbon radical, preferably a 6-10 member aromatic ring system. Preferred aryl groups include, but are not limited to, phenyl, naphthyl, tolyl, and xylyl.

Carboxyl or carboxy means the monovalent group —COOH. Carboxy lower alkyl means —COOR, wherein R is lower alkyl. Carboxy lower alkoxy means —COOROH wherein the R is lower alkyl.

Carbonyl means the group

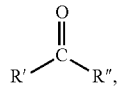

where R' and R" independently can be any of a number of chemical groups including alkyl.

The term "halogen" as used herein means fluorine, chlorine, bromine, or iodine, preferably fluorine and chlorine.

"Hetero atom" means an atom selected from N, O and S.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted.

Hydroxy or hydroxyl is a prefix indicating the presence of a monovalent —O—H group.

"Lower" as in "lower alkenyl" means a group having 1 to 6 carbon atoms.

"Nitro" means —NO₂.

"Oxo" means the group =O.

"Pharmaceutically acceptable," such as pharmaceutically acceptable carrier, excipient, etc., means pharmacologically acceptable and substantially non-toxic to the subject to which the particular compound is administered.

"LCMS" means Liquid Chromatography Mass Spectrometry, i.e. a method for detecting molecular weight of a mixture of compounds, whereby said mixture is first separated into the individual compounds using liquid chromatography, and the molecular weight of said compounds is subsequently detected by mass spectrometry.

The compound (R)-BINAP has the following structure:

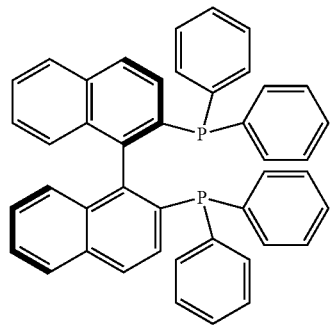

The compound (R)-MeOBIPHEP has the following structure:

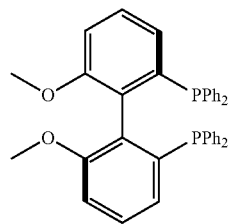

In general, the nomenclature used in this Application is based on AUTONOM™ v.4.0, a Beilstein Institute computerized system for the generation of IUPAC systematic nomenclature.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. In cases where enantiomeric mixtures were separated, stereochemistry may have been assigned, to indicate chiral purity of the final products, but the absolute stereochemistry may not necessarily be confirmed.

It has been found that the products VI obtained from the reaction of (Z)-3-(3-chloro-2-fluoro-phenyl)-4-(4-chloro-2-fluoro-phenyl)-acrylonitrile (Compound IV) with an ester of (E)-4-[2-(3,3-dimethylbutylideneamino)acetamide]-3-methoxybenzoic acid (Compound V) undergo base-catalyzed isomerization to give the compound VII as the major product as shown in Scheme 2. Hydrolysis of the ester of V gave the racemate of Compound I.

Scheme 2

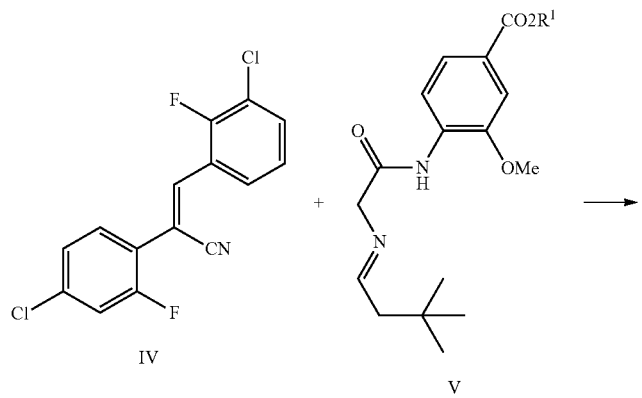

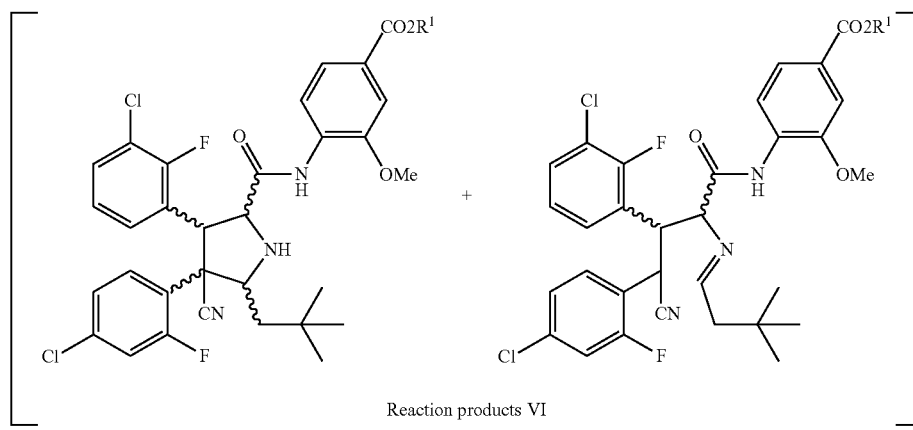

Reaction products VI base catalyzed isomerization

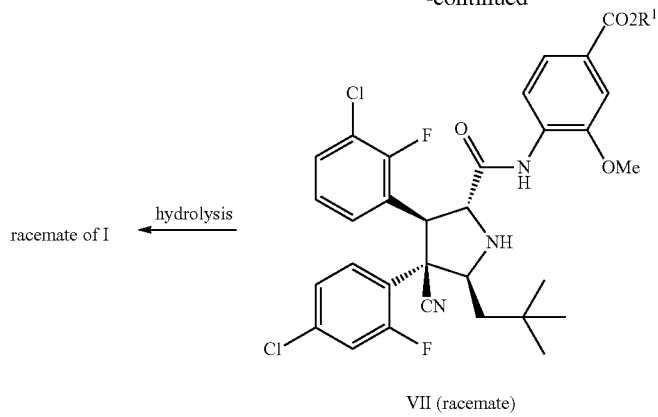

VII (racemate)

$R^1$ in scheme 2 is a non-tertiary alkyl or benzyl or other ester protecting group. Preparation of Compound IV was reported in U.S. patent application Ser. No. 12/702,402.

The synthesis of Compound V is outlined in Scheme 3. Method 1 was previously reported in WO 2012/022707 for the preparation of the corresponding methyl ester of Compound V. Intermediate X can be isolated as a salt, for an example as the hydrochloride salt.

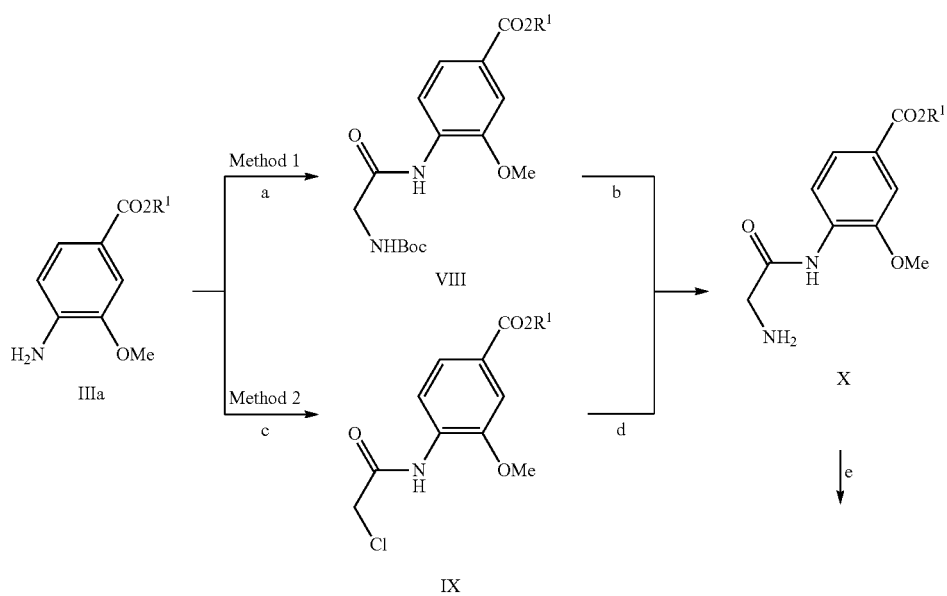

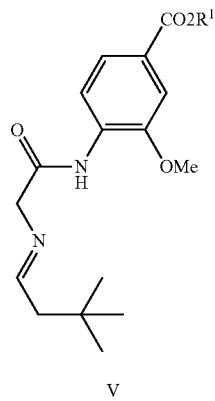

V

Reagents and conditions
a. N-protected glycine, carboxylic acid activating reagent
b. N-protecting group removal conditions compatible with amide and ester
c. Haloacetyl halide (eg. Chloroacetyl chloride or bromoacetyl bromide), base
d. Ammonia or ammonium hydroxide, polar aprotic solvent, less than 30° C.
e. 3,3-Dimethyl butyraldehyde, base (eg. tertiary amine)

According to the present invention, the use of a chiral catalyst in the reaction of Compound IV with Compound V may result in some chiral induction at the "C-3" position of the reaction products, i.e. compounds VI, as shown in Scheme 4. The subsequent base-catalyzed isomerization could then provide enantiomerically enriched product VIIa if the newly established chiral center at the "C-3" position would not suffer from epimerization. This was proven to be the case. Recrystallization of the enantiomerically enriched product VIIa was found to provide enantiomerically pure Compound VIIa. Alternatively, after hydrolysis of the enantiomerically enriched product VIIa, the enantiomeric purity of Compound I was surprisingly readily upgraded by selective precipitation and removal of the racemate of Compound I either as the acid form or as a salt, such as the lithium salt.

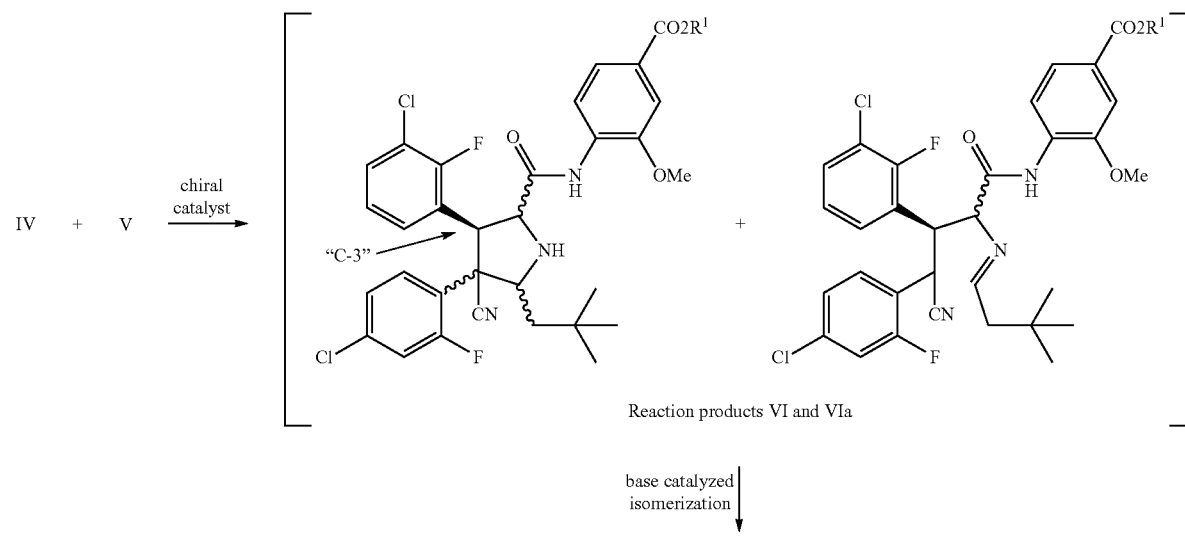

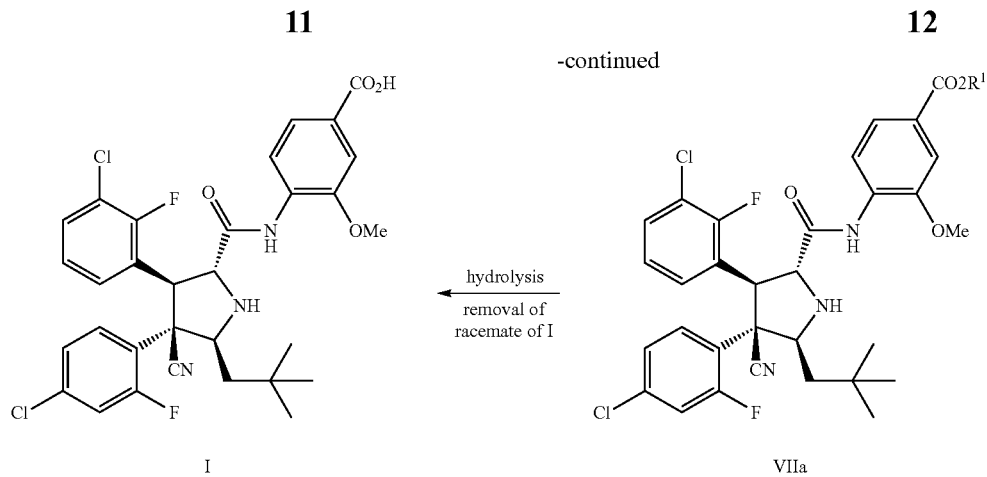

Two distinct chiral catalysis systems using silver and copper, respectively, were found to be particularly effective. The new processes based on these chiral catalysis systems are operationally more simple, have higher throughput, higher overall yield and are more robust and reproducible.

Therefore, in one embodiment, there is provided a process for the production of compound (I)

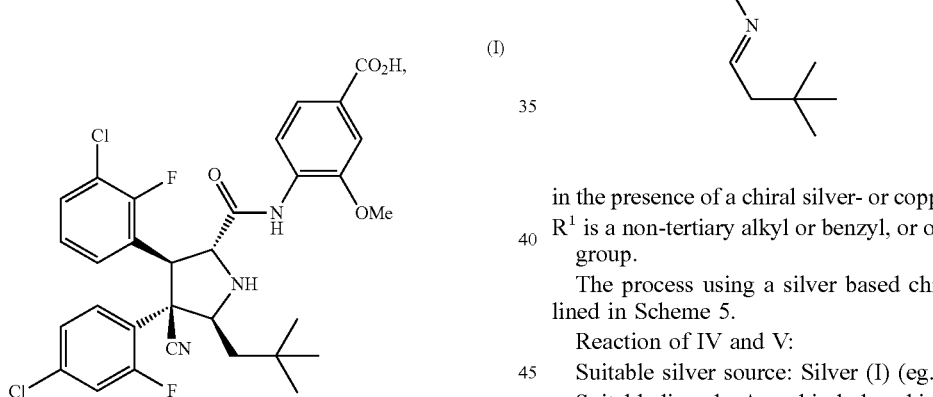

which comprises reacting a compound of the formula (IV)

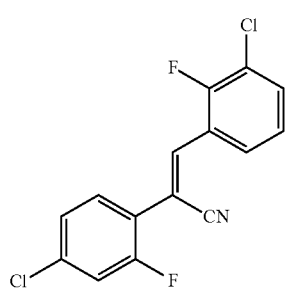

with a compound of the formula (V)

in the presence of a chiral silver- or copper catalyst; wherein $R^1$ is a non-tertiary alkyl or benzyl, or other ester protecting group.

The process using a silver based chiral catalysis is outlined in Scheme 5.

Reaction of IV and V:
Suitable silver source: Silver (I) (eg. silver acetate).
Suitable ligands: Any chiral phosphine or bidentate phosphine (eg. $PPh_3$, R- or S-BINAP, R-BINAP, R- or S-MeOBIPHEP), or other chiral ligand able to coordinate with silver metal.
Suitable solvents: Non-polar, aprotic solvents (eg. THF, Me-THF, Toluene).
Suitable base: None, or a non-nucleophilic amine.
Suitable temperature range: about −10 to about 20° C.
Isomerization to VIIa:
Suitable base: Strong amines (eg. DBU); or with heterogeneous conditions: an insoluble base, such as, anhydrous LiOH.
Suitable solvents: Non-polar, aprotic solvents (eg. THF, Me-THF, Toluene)
Temperature range: about 20 to about 80° C.
Hydrolysis and Isolation of Compound I
Suitable base: Any hydroxide.
Suitable solvents: Any solvent with water miscibility, eg. Alcohols, THF.
Temperature range: about 20 to about 80° C.

Scheme 5

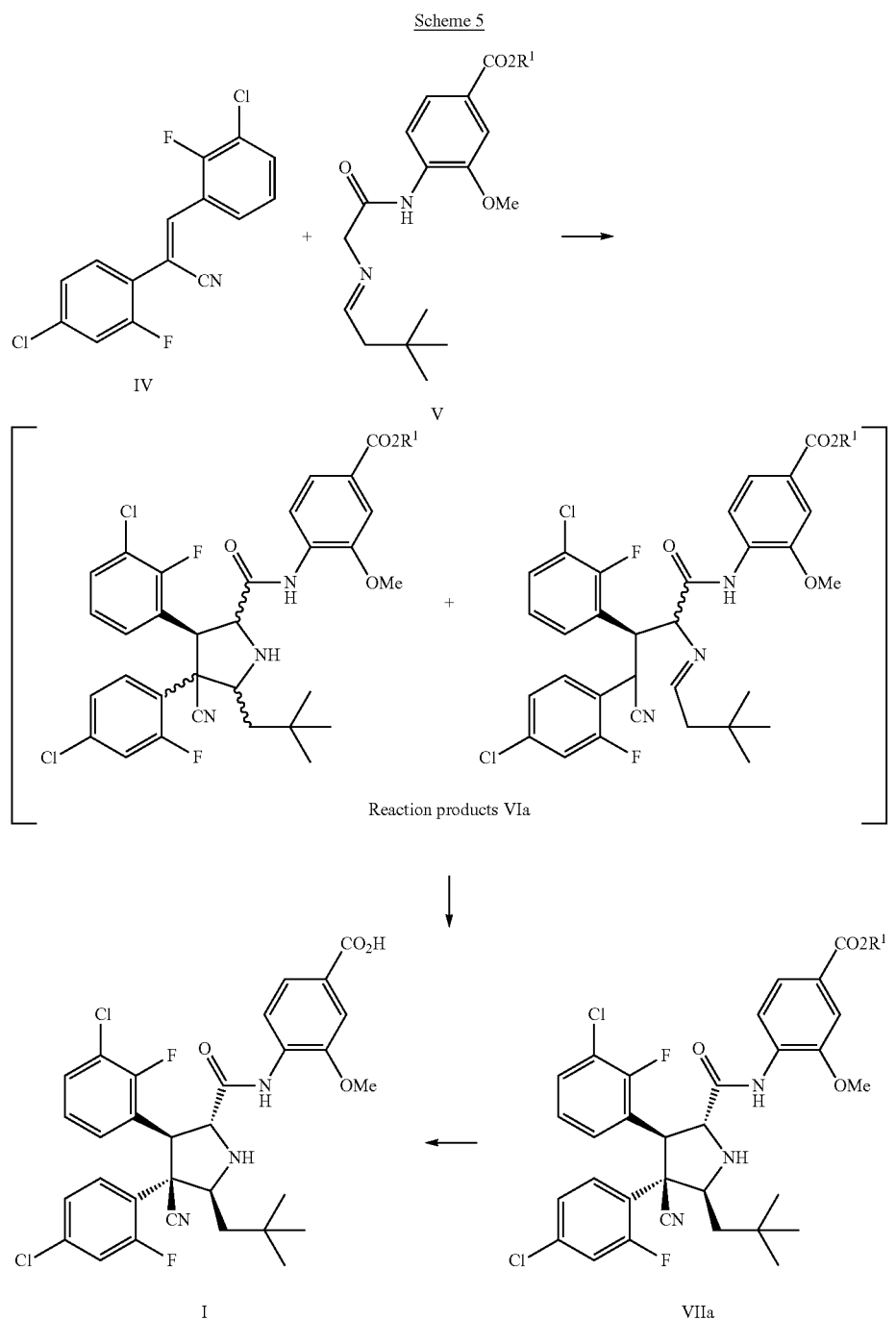

Reaction products VIa

The silver catalyzed asymmetric reaction of Compound IV and Compound V gave a complex mixture of products VIIa, but higher overall yields of compound (I) (based on compound IV) when compared to the reaction procedure as disclosed in scheme 1 above. LCMS analysis of the reaction indicated that most of the products have the expected molecular weight.

Therefore, in one embodiment there is provided the method for making compound (I), comprising reacting a compound of formula (IV) and (V) as disclosed above, wherein the chiral silver catalyst is selected from a complex formed by silver (I) acetate together with a chiral phosphine or bidentate phosphine, such as $PPh_3$, R- or S-BINAP, R-BINAP, R- or S-MeOBIPHEP.

In yet another embodiment, the chiral silver catalyst is selected from a complex formed by silver (I) acetate together with R- or S-BINAP.

In yet another embodiment, the chiral silver catalyst is selected from a complex formed by silver (I) acetate together with R- or S-MeOBIPHEP.

In yet another embodiment, $R^1$ is methyl or ethyl.

In another embodiment, there is provided a process to produce a compound of the formula

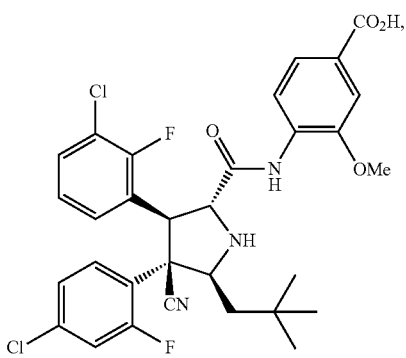

which comprises a) reacting a compound of the formula (IV)

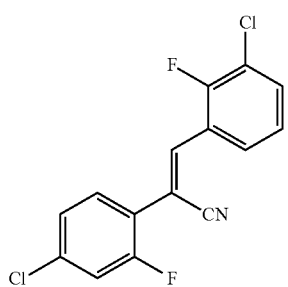

with a compound of the formula (V)

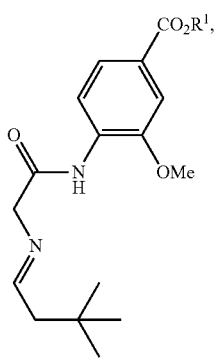

in the presence of a silver catalyst;

b) isomerising the product of (a) by reaction with a suitable base selected from a strong amine or with an insoluble base in the above solvents at a temperature range of from about 20 to 80° C.; and c) hydrolyzing the product of (b) in any suitable hydroxide in a solvent having water miscibility at a temperature between about 20 to about 80° C. to obtain a compound of formula I; wherein $R^1$ is a non-tertiary alkyl or benzyl, or other ester protecting group.

Within this embodiment, there is provided the above process wherein, $R^1$ is methyl or ethyl. Also within this embodiment, the silver catalyst in step a) is silver (I) acetate in combination with any ligand able to coordinate with silver metal. In a preferred embodiment, ligands are chiral phosphine or bidentate phosphine ligands selected from PPh3, R- or S-BINAP, R-BINAP, R- or S-MeOBIPHEP. In a more preferred embodiment, the ligands are R- or S-MeOBIPHEP. Suitable solvents within step a) are non-polar, aprotic solvents such as for example THF, Me-THF or Toluene. The reaction of step a) is carried out in the absence of a base or in the presence of non-nucleophilic amines and at a temperature ranging from about −10 to about 20° C.

In another embodiment there is provided the above process, wherein the insoluble base in step b) is anhydrous LiOH; and the "suitable hydroxide" in c) is aqueous sodium hydroxide (NaOH).

The process using a copper based chiral catalysis is outlined in Scheme 6.

Reaction of IV and V:

Suitable copper source: Copper (I) or Copper (II) (eg. Copper(I) acetate)

Suitable ligands: Any chiral phosphine or bidentate phosphine (eg. PPh$_3$, R- or S-BINAP, R-BINAP, R- or S-MeOBIPHEP), or other chiral ligand able to coordinate with copper metal.

Suitable solvents: Non-polar, aprotic solvents (eg. THF, Me-THF, Toluene).

Suitable base: None, or a non-nucleophilic amine.

Suitable temperature range: about 0 to about 40° C.

Hydrolysis/Isomerization to Compound I

Suitable base: Any hydroxide.

Suitable solvents: Any solvent with water miscibility, eg. Alcohols, THF.

Temperature range: about 20 to about 80° C.

Scheme 6

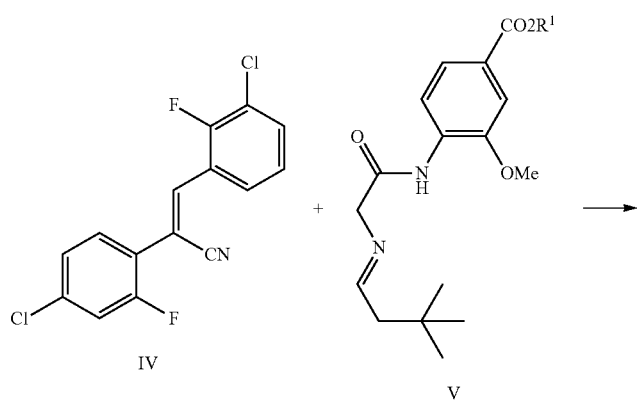

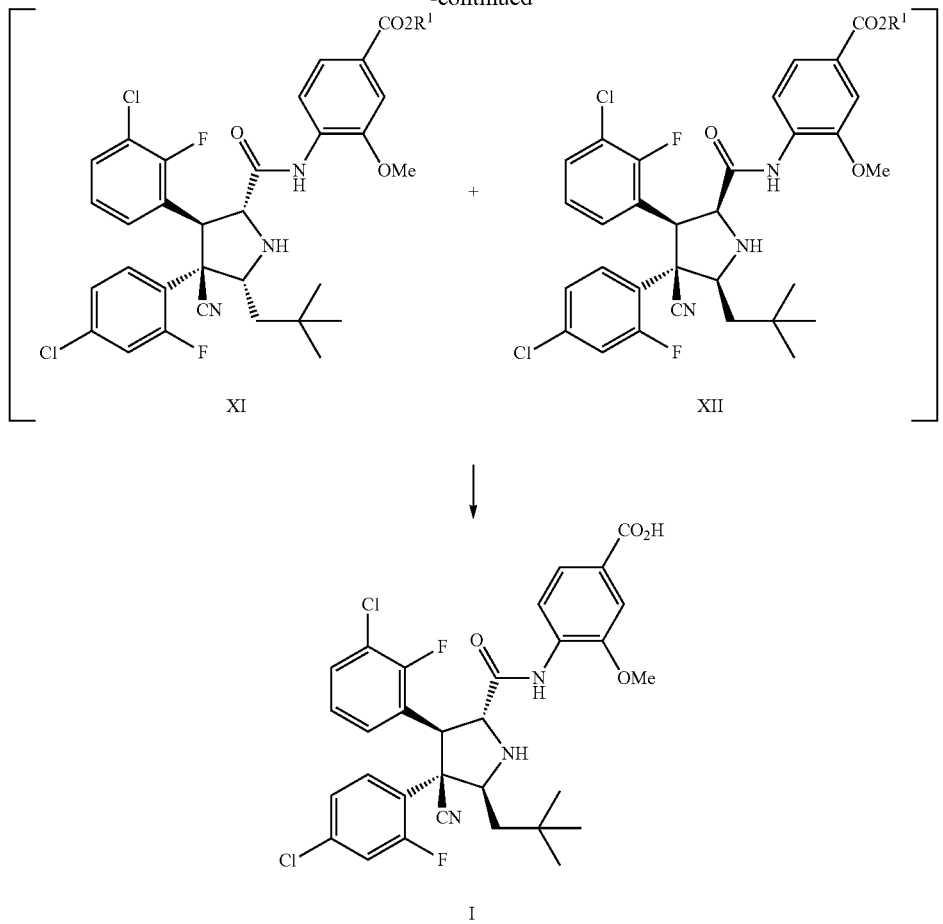

The copper catalyzed asymmetric reaction of Compound IV and Compound V gave a quite different product profile as compared to the reaction using a silver based catalyst, and even higher overall yields of up to about 69% of compound (I) based on (IV). The reaction mainly generated two isomers, Compound XI and Compound XII. These isomers were found to undergo epimerization under the hydrolysis conditions to give Compound I.

Since the exo product (compound XI) can be obtained in high enantiopurity and is a known precursor of compound (I), it has been another object of the present invention to improve formation of this isomer during the [3+2] cycloaddition step a). Therefore, screening studies were conducted using compounds IV and V wherein $R^1$ is methyl and ethyl. However, the choice of any one of these groups had no impact on the selectivities for the products. The data shown in Table 1 below were obtained with $R^1$ being ethyl (Et). For the screening, the reactions were carried out under nitrogen atmosphere with 1 or 2 mol % of Cu(OAc)$_2$ as catalyst and (R)-BINAP as ligand in 6 volumes of solvents. Since lowering the reaction temperature to 0° C. resulted in significantly slower reaction rate without any beneficial effect for the selectivities, all reactions were run at room temperature.

The screening studies started with investigation of a solvent effect, and THF, MeTHF, CPME, dichlormethane, and toluene were examined. Poor selectivity (~45 area %) for the exo isomer was obtained in dichloromethane. In CPME, MeTHF and toluene, the reactions gave the exo adducts in ~80 area % as compared to ~75 area % for reactions in THF. MeTHF was selected for further investigation as the reaction is faster in this solvent than in CPME and toluene.

The reaction of (IV) with (V) ($R^1$=Et, 3) proceeded slower in the absence of base, and HPLC analysis showed higher level of unidentified intermediates. The formation of these intermediates was partially suppressed with catalytic amount of base. Three bases, triethylamine, DIPEA, and DABCO, were tested and worked equally well. One equivalent of the base was sufficient for the reaction to complete in 24 h, and no further improvement was observed when excess amount of base was used.

Since both Cu(I) and Cu(II) salts are able to catalyze the [3+2] cycloaddition in the absence of a ligand, it is important to pre-form the metal/ligand complex to minimize the background reactions. Normally, Cu(OAc)$_2$ and (R)-BINAP were mixed in MeTHF and stirred for 2 to 3 h before the addition of the substrates. Under these conditions, in the crude mixture, the ratio of exo:endo was ~10:1. Short catalyst aging (eg. <30 min) led to incomplete reaction and poor exo:endo selectivity (~3:5). On the contrary, longer catalyst aging (eg. 20 h) resulted in faster reaction (7 h vs overnight) and an improved exo:endo ratio of ~20:1. However, the total percentage of the minor isomers remained at 10-12 area %. The improved exo:endo ratio did not lead to a better isolated yield for compound (I) at the end.

The ligand screening was conducted with Cu(OAc)$_2$ (1.0 mol %), phosphine ligand (1.1 mol %) and N,N-diisopropylethylamine (DIPEA, 1 equiv) in MeTHF at room temperature for 2 days to ensure complete conversion achieved. All reactions gave compound (XI) or (XII) ($R^1$=Et) as the major products (Table 1), though level of other minor isomers varied slightly. The reaction mixtures were then treated with aqueous sodium hydroxide (NaOH) to convert both compound (XI) and (XII) ($R^1$=Et; 6 and 7) to compound (I). The resulting mixture was analyzed by chiral HPLC.

As summarized in Table 1, generally reactions with better selectivity for the exo isomer compound (XI) ($R^1$=Et, 6) (entries 1, 3, 5-7, 14-18) also gave higher ee for compound (I). The best ee obtained was 90.7% (entry 3) with entry 3 (ligand 22), as compared to 89.0% ee with (R)-BINAP (entry 18). However, the increase in enantioselectivity is only minor, and ultimately ligand 22 has other disadvantages (i.e costs) when used in large industrial scale production.

TABLE 1

HPLC result of the ligand screening

| entry | ligand | HPLC area XI:XII | ee of compound (I) after hydrolysis/isomerization |
|---|---|---|---|
| 1 | 20 | 91:9 | 80.8 |
| 2 | 21 | 29:71 | 25.4 |
| 3 | 22 | 94:6 | 90.7 |
| 4 | 23 | 9:91 | 39.8 |
| 5 | 24 | 90:10 | 83.2 |
| 6 | 25 | 94:6 | 83.8 |
| 7 | 26 | 94:6 | 86.3 |
| 8 | 27 | 86:14 | 66.4 |
| 9 | 28 | 10:90 | 77.9 |
| 10 | 29 | 47:53 | −20.0 |
| 11 | 30 | 56:44 | −58.0 |
| 12 | 31 | 68:32 | 60.0 |
| 13 | 32 | 86:14 | 71.3 |
| 14 | 33 | 90:10 | 83.0 |
| 15 | 11 | 93:7 | 84.0 |
| 16 | 34 | 91:9 | 84.8 |
| 17 | 35 | 92:8 | 86.0 |
| 18 | (R)-BINAP | 91:9 | 89.0 |

$R^1$ in compounds (XI) and (XII) is ethyl (Et). These compounds are designed 6 and 7, respectively in Example 5. Compound (I) is designated as 5 in Example 4, 5 and 6. Chemical Structures of ligands are shown in FIG. 1.

Therefore, in one embodiment, there is provided a process for the production of compound (I)

which comprises reacting a compound of the formula (IV)

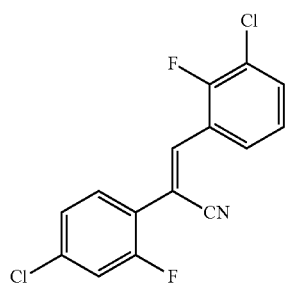

(IV)

with a compound of the formula (V)

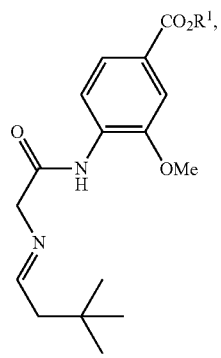

(V)

in the presence of a chiral copper catalyst; wherein
$R^1$ is a non-tertiary alkyl or benzyl, or other ester protecting group.

In another embodiment, the chiral copper catalyst is selected from a complex formed by copper (I) acetate together with a chiral phosphine or bidentate phosphine, such as PPh$_3$, R- or S-BINAP, R-BINAP, R- or S-MeOBI-PHEP.

In yet another embodiment, the chiral copper catalyst is selected from a complex formed by copper (I) acetate together with R- or S-BINAP.

In yet another embodiment, the chiral copper catalyst is selected from a complex formed by copper (I) acetate together with R-BINAP.

In another embodiment, $R^1$ in the copper catalyzed formation of compound (I) is a linear alkyl selected from methyl, ethyl, propyl or butyl; preferably methyl or ethyl.

In another embodiment, there is provided a process to produce a compound of the formula (I)

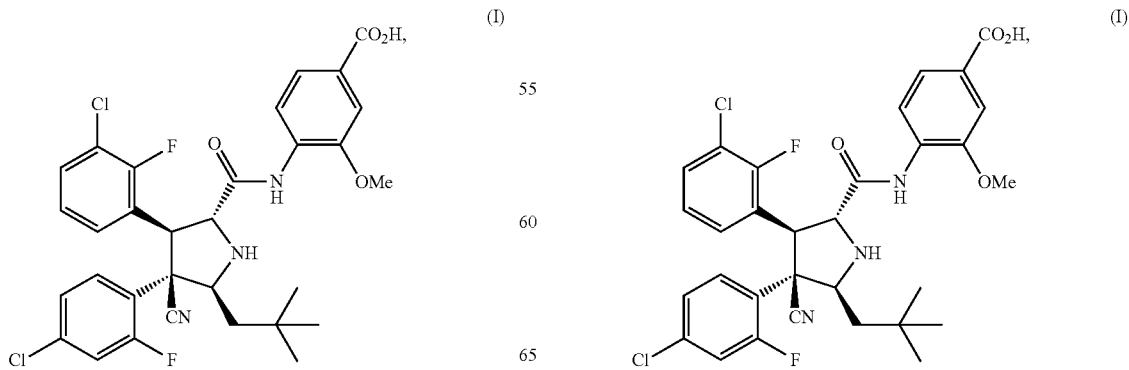

which comprises reacting a compound of the formula (IV)

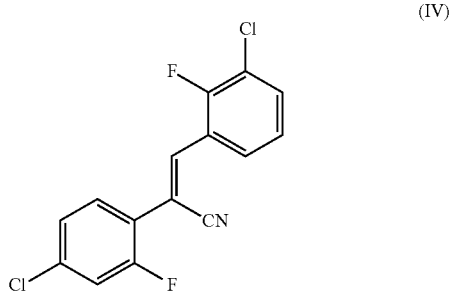 [SMILES: N#C/C(=C\c1cccc(Cl)c1F)c1ccc(Cl)cc1F]

with a compound of the formula (V)

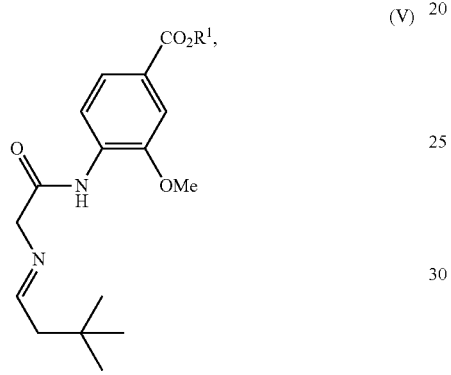

in the presence of a suitable copper source;

b) isomerising the product of (a) by reaction with a suitable base selected from a strong amine or with an insoluble base in the above solvents and at the above temperature range and;

c) hydrolyzing the product of (b) in a suitable hydroxide in a solvent having water miscibility at a temperature of about 20° C. to about 80° C. to obtain a compound of formula I; wherein $R^1$ is a non-tertiary alkyl or benzyl, or other ester protecting group.

Within this embodiment, the copper source in process step a) is Copper (I) or Copper (II) such as for example Copper (I) acetate, in combination with any chiral phosphine or bidentate phosphine or other chiral ligand able to coordinate with copper metal. Also, within this embodiment said ligands are preferably selected from $PPh_3$, R- or S-BINAP, R-BINAP, R- or S-MeOBIPHEP. In a more preferred embodiment the ligand is selected from R- or S-BINAP.

In another embodiment, there is provided the above process wherein the copper source in step a) is a chiral copper catalyst prepared from a complex consisting of copper (I) acetate and the ligand R-BINAP, and reaction step a) is carried out in a non-polar or aprotic solvent together with optionally a base selected from triethylamine, N,N-diisopropylethylamine (DIPEA) or 1,4-Diazabicyclo[2.2.2]octane (DABCO); in a temperature range of about 0° C. to about 40° C. Within this embodiment the use of DIPEA is especially preferred.

In another embodiment, there is provided the above copper catalyzed reaction sequence a) to c) wherein the insoluble base in reaction step b) is anhydrous LiOH.

In another embodiment, there is provided the above copper catalyzed reaction sequence a) to c) wherein the suitable hydroxide in reaction step c) is aqueous NaOH.

In another embodiment, there is provided a process to produce a compound of the formula (I) as defined above, which comprises a) reacting a compound of the formula (IV)

with a compound of the formula (V)

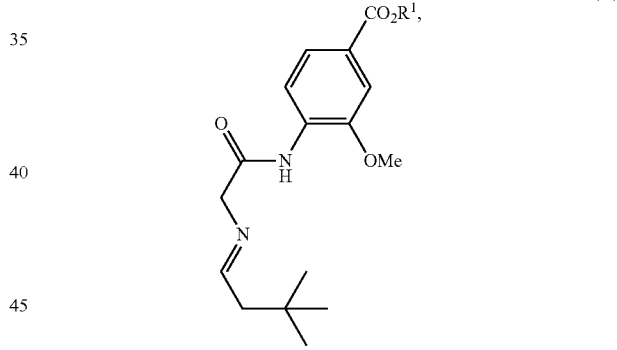

in the presence of a catalyst formed by copper (I) acetate and R-BINAP in MeTHF; optionally in the presence of N,N-diisopropylethylamine (DIPEA) and at a temperature within the temperature range of about 0° C. to about 40° C.;

b) isomerising the product of (a) by reaction with a suitable base selected from a strong amine or with an insoluble base in the above solvents and at the above temperature range and;

c) hydrolyzing the product of (b) in a suitable hydroxide in a solvent having water miscibility at a temperature of about 20° C. to about 80° C. to obtain a compound of formula I; and wherein $R^1$ is methyl or ethyl.

Compounds of the formulae (6) and (7) are intermediates in the method according to the present invention. Therefore, in yet another embodiment, there is provided the compound of the formula (6)

In another embodiment, there is provided the intermediate compound of the formula (7)

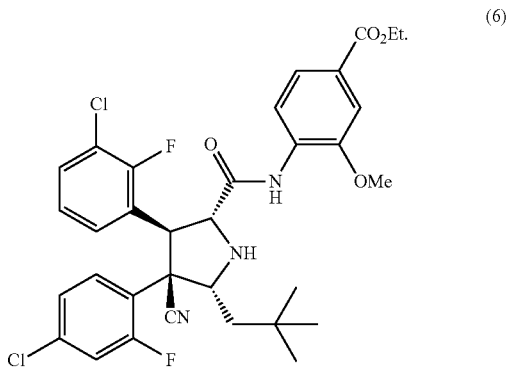 [SMILES: CCOC(=O)c1ccc(NC(=O)[C@@H]2N[C@H](CC(C)(C)C)[C@](C#N)(c3ccc(Cl)cc3F)[C@H]2c2cccc(Cl)c2F)c(OC)c1]

(6)

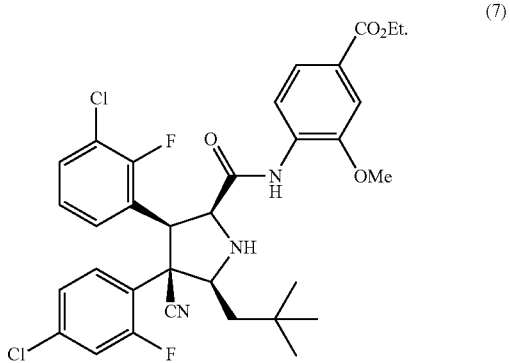 [SMILES: CCOC(=O)c1ccc(NC(=O)[C@H]2N[C@@H](CC(C)(C)C)[C@](C#N)(c3ccc(Cl)cc3F)[C@H]2c2cccc(Cl)c2F)c(OC)c1]

(7)

In another embodiment, there is provided a pharmaceutical preparation comprising a compound of formula (I) produced by any of the silver-catalysed processes as disclosed above together with a pharmaceutically acceptable excipient and/or carrier.

In another embodiment, there is provided a pharmaceutical preparation comprising a compound of formula (I) produced by any of the copper-catalysed processes as disclosed above together with a pharmaceutically acceptable excipient and/or carrier.

The invention is now illustrated by the following working examples.

EXAMPLES

Example 1

(Z)-3-(3-Chloro-2-fluoro-phenyl)-2-(4-chloro-2-fluoro-phenyl)-acrylonitrile

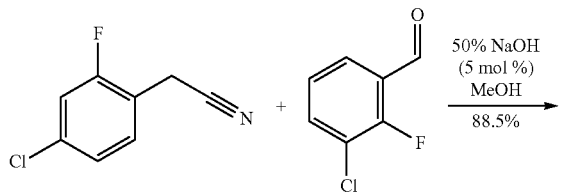

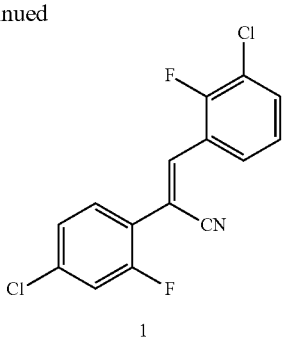

1

A 250-L glass-lined reactor was charged with 2-(4-chloro-2-fluorophenyl)acetonitrile (15.0 kg, 88.5 mol, Eq: 0.988), 3-chloro-2-fluorobenzaldehyde (14.2 kg, 89.6 mol, Eq: 1.00), MeOH (140 L). In one portion, a solution of sodium hydroxide [prepared from 50 wt % solution (0.23 L, 4.4 mmol, Eq: 0.05) diluted in methanol (10 L)] was added. The resulting mixture was heated to 50° C. for 4.5 h, and then the resulting thick slurry was cooled down to 20° C. Consumption of 3-chloro-2-fluorobenzaldehyde was monitored by HPLC analysis. The solid product was isolated by filtration via a 0.3 m² filter/dryer and the cake washed with methanol (58 L). The product was dried under vacuum with N2 purge at 60° C. to provide the stilbene as a white powder, 24.2 kg (88.5% yield) with 99.87% purity by HPLC analysis.

$^1$H NMR (300 MHz, CDCl$_3$) δ 8.10-8.15 (1H, m), 7.79 (1H, s), 7.48-7.59 (2H, m), 7.20-7.28 (3H, m).

Example 2

(E)-ethyl 4-(2-(3,3-dimethylbutylideneamino)acetamido)-3-methoxybenzoate

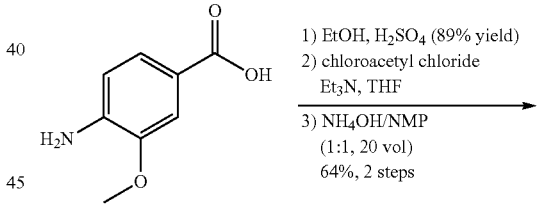

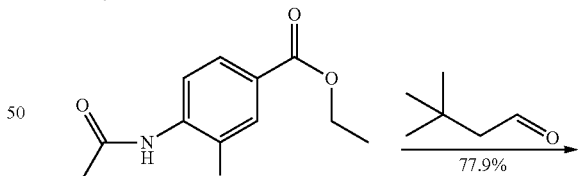

2

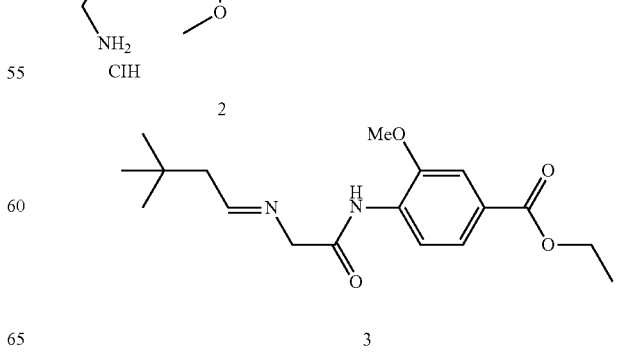

3

Ethyl 4-amino-3-methoxybenzoate

A 22-L 3-necked RBF equipped with an electrical heating mantle, a thermocouple probe, overhead mechanical stirrer, water-cooled condenser, nitrogen bubbler and addition funnel was charged with 4-amino-3-methoxybenzoic acid (1.0 kg, 5.98 mol, 1.0 equiv.) and ethanol (200 proof) (10.0 L, 10 vol.) to produce a stirrable slurry. Without external cooling, sulfuric acid (1.17 kg, 0.64 L, 12.0 mol, 2.0 equiv.) was then added slowly over 1 h, the slurry initially goes thick, but breaks up and eventually all solids dissolve to form a dark solution. The exothermic addition increased the temperature to ~45° C.; additional heating was then applied to bring the solution to reflux and was held at reflux overnight. An HPLC sample was taken and showed ~5% starting benzoic acid remaining. The reflux head was switched to full takeoff and 2.5 L was distilled off. The reaction was cooled to 6° C. in an ice bath and the pH slowly adjusted to 12 by the addition of a solution of sodium hydroxide (50 wt %, 1.03 kg, 681 ml, 12.9 mol, 2.15 equiv.) in water (3.5 L) keeping the temperature below 20° C. Following a 30 min. post-stir, an additional quantity of water (4.0 L) was added and stirred at ca. 10° C. for 30 min. The solid were filtered, washed thoroughly with water (4.0 L), and then vacuum dried at 65° C. overnight. The yield of ethyl 4-amino-3-methoxybenzoate was 1.04 kg (89.1%) as a light brown solid.

m.p.=83-87° C. (DSC); $^1$H NMR (300 MHz, CDCl$_3$) δ 7.56 (1H, dd, J=7.9, 1.5 Hz), 7.47 (1H, d J=1.5 Hz), 6.66 (1H, d, J=7.9 Hz), 4.33 (2H, t, J=7.2 Hz), 4.27 (1H, br s), 3.90 (3H), 1.37 (3H, t, J=7.2 Hz).

Ethyl 4-(2-chloroacetamido)-3-methoxybenzoate

In a 12-L 3-necked RBF equipped with an ice-water bath, overhead mechanical stirrer, nitrogen bubbler and addition funnel, was dissolved ethyl 4-amino-3-methoxybenzoate (500 g, 2.56 mol, 1.0 equiv.) in glacial acetic acid (3.15 kg, 3.00 L) at 14° C. in an ice water bath. To this solution was rapidly added 2-chloroacetyl chloride (318 g, 224 ml, 2.82 mol, 1.1 equiv.) over 10 min. with vigorous stirring. The reaction was then allowed to warm to room temperature over 1 h. The reaction was monitored by HPLC. To the cooled solution at 17° C. (ice-water bath) was added over 30 min. a solution of sodium acetate (345 g, 4.2 mol, 1.6 equiv.) in water (3.0 L) with agitation. An initial exotherm raised the temperature to 30.4° C. which rapidly cooled down after ~10% of the aqueous sodium acetate had been added. (Alternatively, a reverse quench of the reaction mixture into the cooled sodium acetate solution can be performed). The product slowly crystallizes from the clear solution, and the mixture progressively thickens over time. The slurry was cooled to ~10° C. and stirred for 1 h. The product was collected by filtration and washed with water (3.0 L) then vacuum dried over night at 65° C. with a nitrogen bleed. Yield of chloroacetanilide was 606 g (87%) as an off-white crystalline solid.

$^1$H NMR (300 MHz, CDCl$_3$) δ 9.11 br s (1H), 8.44 (1H, d, J=8.3 Hz), 7.71 (1H, dd, J=8.5, 1.7 Hz), 7.59 (1H, d, J=1.7 Hz), 4.38 (2H, q, J=7.2 Hz), 4.22 (2H), 3.99 (3H), 1.41 (3H, t, J=7.2 Hz).

Ethyl 4-(2-aminoacetamido)-3-methoxybenzoate hydrochloride

A 22-L 3-necked RBF equipped with an electrical heating mantle, a thermocouple probe, overhead mechanical stirrer, an addition funnel and bubbler was charged with ammonium hydroxide solution (28-30% NH3, 5.0 L, 5 vol., 4.5 kg, 77.8 mol, 42.3 equiv.). Ethyl 4-(2-chloroacetamido)-3-methoxybenzoate (500 g, 1.84 mol, 1.0 equiv.) in N-methylpyrrolidone (5.0 L, 5 vol.) was added over 30 min. to the vigorously agitated ammonium hydroxide solution. Some effervescence from ammonia gas evolution was observed. After warming the reaction mixture to 25° C., it was held for 5 h to complete ammonolysis as determined by HPLC analysis. The clear tea-colored solution was placed under vacuum to degas the excess ammonia. The temperature was not controlled during this step. The reactor system was modified with a Dean-Stark trap, charged with toluene (5.0 L, 5.0 vol) and then heated to 90° C. (at start of drying) to 130° C. (at completion) to remove water via azeotropic distillation a total of 3.5 L water was removed over 8 h to cause the product to crystallize from the NMP/toluene solution. After cooling overnight, the amine hydrochloride was collected by filtration, washed with toluene (1.5 L, 3 vol.) and vacuum dried at 65° C. with a nitrogen bleed. Yield of ethyl 4-(2-aminoacetamido)-3-methoxybenzoate hydrochloride was 391 g (73.5%) as white crystalline needles.

$^1$H NMR (300 MHz, DMSO-d6) δ 10.0 br s (1H), 8.22 (1H, d, J=8.7 Hz), 7.59 (1H, dd, J=8.3, 1.9 Hz), 7.53 (1H, d, J=1.9 Hz), 4.30 (2H, q, J=7.2 Hz), 3.92 (3H), 3.87 (2H), 1.31 (3H, t, J=7.2 Hz).

(E)-ethyl 4-(2-(3,3-dimethylbutylideneamino)acetamido)-3-methoxybenzoate

A 4-L jacketed reactor was charged with ethyl 4-(2-aminoacetamido)-3-methoxybenzoate hydrochloride (150 g, 520 mmol) and MTBE (1.11 kg, 1.5 L). To this slurry was added 3,3-dimethylbutanal (56.2 g, 70.4 ml, 561 mmol, Eq: 1.08) then triethylamine (55.2 g, 76.0 ml, 545 mmol, Eq: 1.05). The resulting slurry was stirred under N$_2$ at 23° C. for 17 h. Consumption of amine was monitored by GC analysis. The mixture was washed with water (2×500 ml) and the organic layer polish filtered. MTBE was replaced with n-heptane by distillation to achieve a solution in 750 mL n-heptane. The solution was cooled to 5° C. and the product was isolated by filtration, and the solid washed with n-heptane, then oven dried at 50° C. under vacuum with N2 purge. The imine 3 was obtained as 135.36 g of crystalline solid (77.9% yield).

$^1$H NMR (300 MHz, CDCl$_3$) δ 9.46 br s (1H), 8.53 (1H, d, J=8.7 Hz), 7.85 (1H, tt, J=5.6, 1.1 Hz), 7.70 (1H, dd, J=8.7, 1.9 Hz), 7.55 (1H, d, J=1.9 Hz), 4.37 (2H, q, J=7.2 Hz), 4.22 (2H, d, J=1.1 Hz), 3.94 (3H), 2.28 (1H, d, J=5.6, 1.40 (3H, t, J=7.2 Hz), 1.04 (9H).

Example 3

Chiral Silver Catalyzed Route to Ester Isomer

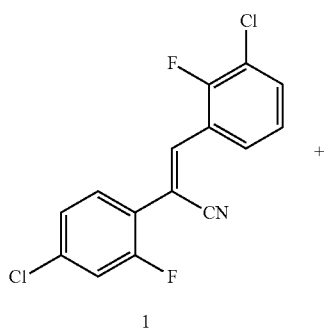

1

-continued

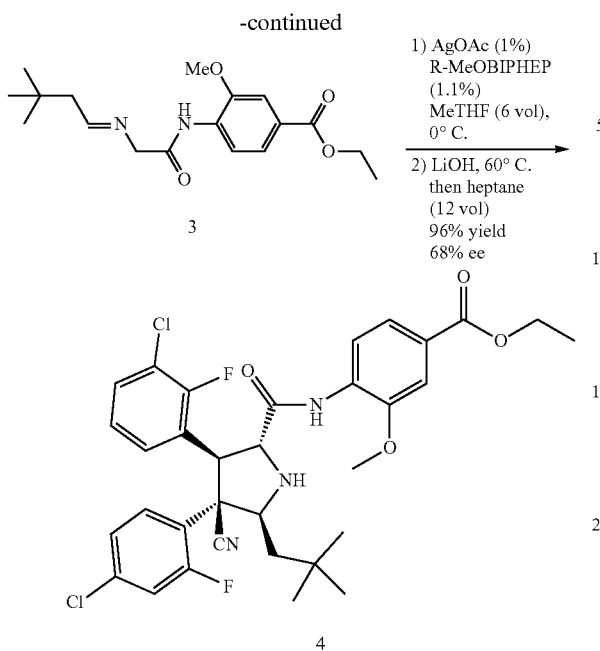

1) AgOAc (1%)
R-MeOBIPHEP (1.1%)
MeTHF (6 vol), 0° C.
2) LiOH, 60° C. then heptane (12 vol)
96% yield
68% ee In a 4-L jacketed reactor equipped with overhead stirring was added (Z)-3-(3-Chloro-2-fluoro-phenyl)-2-(4-chloro-2-fluoro-phenyl)-acrylonitrile (196.04 g, 632 mmol, Eq: 1.00) (1), (E)-ethyl 4-(2-(3,3dimethylbutylideneamino)acetamido)-3-methoxybenzoate (233 g, 695 mmol, Eq: 1.1) (3), R-MeOBIPHEP (4.05 g, 6.95 mmol, Eq: 0.011) followed by 2-methyl tetrahydrofuran (1.18 L). The resulting mixture was stirred and degased by two vacuum/nitrogen purge cycles, then cooled to 0° C. internal temperature. Silver(I) acetate (1.06 g, 6.32 mmol, Eq: 0.01) was added as a solid in one portion and then the mixture stirred at 0° C. (Alternatively, the R-MeOBIPHEP ligand and silver(I) acetate can be premixed to give the metal ligand complex that is poorly soluble in 2-MeTHF but can be easily handled as a slurry). The reaction was monitored by HPLC for consumption of the stilbene starting material 1, while a complex intermediate mixture of products was observed to form. When 1 was consumed, the isomeric mixture was isomerized to a single product by addition of finely powdered anhydrous lithium hydroxide (16.7 g, 695 mmol, Eq: 1.1), and the resulting heterogeneous mixture stirred at 60-65° C. for 24 h. The reaction was monitored by HPLC for conversion of the complex reaction mixture into a single isomer (which crystallized from the reaction mixture). N-heptane (2.35 L) was added and the slurry cooled to 15° C. The precipitated mixture of lithium hydroxide and ester 4 was isolated by filtration and the cake washed with 2:1 n-heptane:MeTHF (1.8 L). The solid was vacuum oven dried at 50° C. to give 391.28 g of solid (96% yield). This solid contained the ester isomer 4, with 99.48% purity by HPLC analysis and an enantiomeric ratio of ~84:16 (68% ee) by chiral HPLC analysis, but co-precipitated lithium hydroxide was also present (not quantified).

Compound 4: $^1$H NMR (400 MHz, DMSO-$d_6$) δ: 10.52 (s, 1H), 8.39 (br. s., 1H), 7.74 (t, J=6.9 Hz, 1H), 7.49-7.65 (m, 4H), 7.27-7.47 (m, 3H), 4.61 (d, J=6.3 Hz, 2H), 4.39 (br. s., 1H), 4.31 (q, J=7.0 Hz, 2H), 3.96-4.04 (m, 1H), 3.92 (br. s., 3H), 1.65 (dd, J=13.7, 9.9 Hz, 1H), 1.33 (t, J=7.2 Hz, 3H), 1.27 (d, J=14.3 Hz, 1H), 0.98 (s, 9H).

Example 4

Hydrolysis of Ester and Isolation of Enantiopure Acid

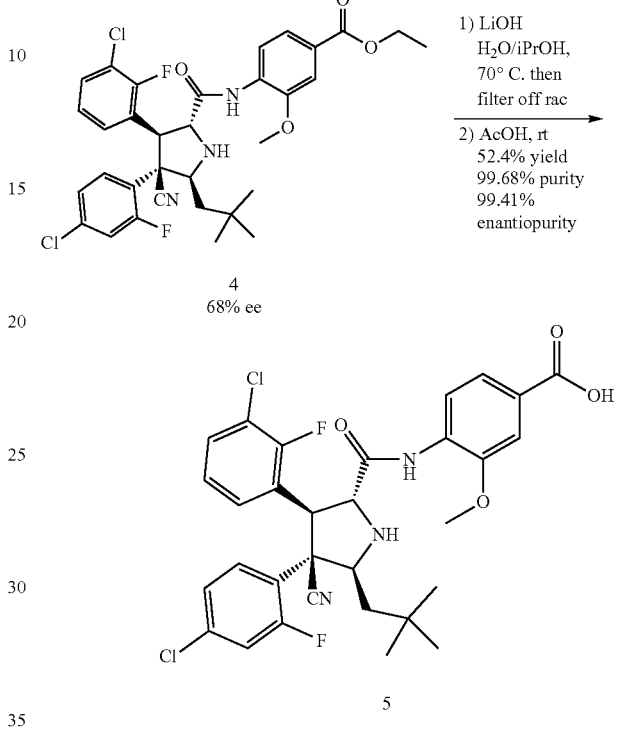

1) LiOH H$_2$O/iPrOH, 70° C. then filter off rac
2) AcOH, rt
52.4% yield
99.68% purity
99.41% enantiopurity Ester 4 (115.18 g, 179 mmol, also containing theoretically 1.1 mole eq. of co-precipitated LiOH) was suspended in 2-propanol (576 mL). A solution of lithium hydroxide (856 mg, 35.7 mmol, 0.2 eq) in water (115 mL) was added, and the stirred mixture was heated at 65° C. under N$_2$ atmosphere overnight. The hydrolysis was monitored by HPLC analysis. When hydrolysis was complete the reaction mixture was cooled to 15° C. The suspended solids (racemic lithium salt of 5) were removed by filtration, and the filter cake washed with 2-propanol (384 ml). The liquors, containing the entantioenriched lithium salt of 5, were polish filtered into a clean 4-L jacketed reactor equipped with overhead stirring, and further diluted with 2-propanol (191 mL). The clear yellow solution was heated to 70° C. and then acetic acid (23.6 g, 22.5 ml, 393 mmol, Eq: 2.2) added in one portion. Crystallization occurred after a few minutes and the mixture became thick with solids in yellow liquors. The suspension was aged at 70° C. for 1 hour and then water (864 mL) was added slowly over ~20 min. The batch temperature was returned to 70° C. and then the batch slowly cooled to 10° C. The product was isolated by filtration and cake washed with 1:1 2-propanol:water (864 mL). After vacuum oven drying at 50° C., acid 5 was obtained as 57.7 g of white crystalline solid (52.4% yield), with 99.68% purity by HPLC, 99.41% enantiopurity by chiral HPLC.

Compound 5: $^1$H NMR (400 MHz, DMSO-$d_6$) δ: 12.89 (br. s., 1H), 10.50 (s, 1H), 8.39 (d, J=8.8 Hz, 1H), 7.75 (t, J=6.8 Hz, 1H), 7.51-7.64 (m, 4H), 7.33-7.46 (m, 3H), 4.57-4.66 (m, 2H), 4.36-4.47 (m, 1H), 3.95-4.03 (m, 1H), 3.94 (s, 3H), 1.66 (dd, J=14.2, 9.9 Hz, 1H), 1.28 (d, J=13.8 Hz, 1H), 0.99 (s, 9H).

Example 5

Chiral Copper Catalyzed Route to Compound (I) with R¹=Ethyl (5)

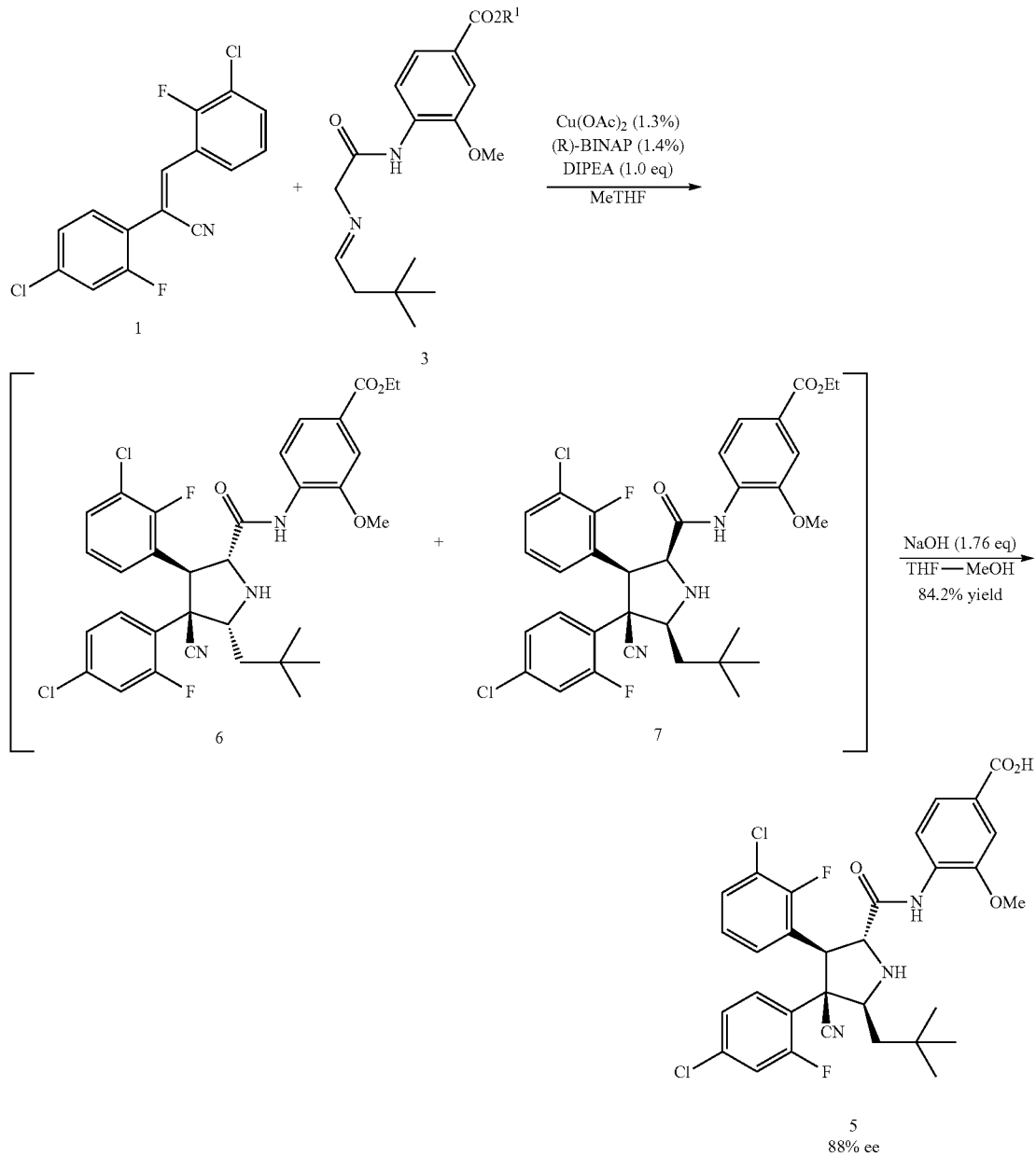

A 500-mL, round bottomed flask equipped with a magnetic stirrer and nitrogen inlet/bubbler was charged with copper(II) acetate (150 mg, 0.826 mmol), (R)-BINAP (560 mg, 0.899 mmol), and 2-methyltetrahydrofuran (120 mL). The suspension was stirred at room temperature under $N_2$ for 3 h when a clear blue solution was obtained. Then 12.0 mL (68.7 mmol) of N,N-diisopropylethylamine was added, followed by 20.0 g (64.5 mmol) of Compound (1) and 24.0 g (71.8 mmol) of Compound (2). The suspension was stirred at room temperature under $N_2$ for 18 h, and LCMS analysis indicated complete reaction. The reaction mixture was diluted with 100 mL of 5% ammonium acetate solution and stirred for 15 min, then poured into a 500-mL separatory funnel. The organic phase separated was washed with an additional 5% ammonium acetate solution (100 mL), then with 100 mL of 5% sodium chloride solution (100 mL), and concentrated at 40° C. under reduced pressure to a thick syrup (ca. 60 g). This syrup (containing 6 and 7) was dissolved in tetrahydrofuran (120 mL), methanol (60.0 mL), and water (6.00 mL). Then sodium hydroxide (50% solution, 6.00 mL, 114 mmol) was added dropwise. The mixture was stirred at room temperature for 18 h. LCMS and chiral HPLC indicated complete hydrolysis and isomerization. The reaction mixture was acidified with 20.0 mL (349 mmol) of acetic acid, and then concentrated at 40° C. under reduced pressure to remove ca. 80 mL of solvent. The residue was diluted with 2-propanol (200 mL), and further concentrated to remove ca. 60 mL of solvent, and then water (120 mL) was added. The slurry was stirred under reflux for 1 h, at room temperature overnight, then filtered and the flask was rinsed with of 2-propanol-water (2:1) (20.0 mL). The filter cake was washed with 2-propanol-water (1:1) (2×100 mL=200 mL), and with water (2×200 mL=400 mL), then vacuum oven dried at 60° C. to give 33.48 g (84.2% yield) of crude Compound 5 as a white solid; 99.26% pure and 87.93% ee as judged by LCMS and chiral HPLC analysis.

Compound 6 (exo cycloaddition product, 2,5-cis): $^1$H NMR (400 MHz, CDCl$_3$) δ 9.66 (brs, 1H), 8.42 (d, J=8.3 Hz, 1H), 7.89 (m, 1H), 7.65 (dd, J=8.6, 1.8 Hz, 1H), 7.55 (d, J=1.8 Hz, 1H), 7.40 (m, 1H), 7.32 (td, J=8.3, 1.5 Hz, 1H), 7.22-7.15 (m, 3H), 4.45 (m, 2H), 4.36 (q, J=7.2 Hz, 2H), 4.25 (m, 1H), 3.91 (s, 3H), 1.39 (t, J=7.2 Hz, 3H), 1.30 (dd, J=14.2, 9.3 Hz, 1H), 0.92 (s, 9H), 0.84 (d, J=14.2 Hz, 1H).

Compound 7 (endo cycloaddition product, 2,5-cis): $^1$H NMR (400 MHz, CDCl$_3$) δ 9.97 (brs, 1H), 8.30 (d, J=8.4 Hz, 1H), 7.65 (dd, J=8.3, 1.8 Hz, 1H), 7.56 (d, J=1.7 Hz, 1H), 7.51 (m, 1H), 7.43 (t, J=8.4 Hz, 1H), 7.23 (m, 1H), 7.17 (dd, J=12.6, 2.0 Hz, 1H), 7.11 (m, 1H), 6.89 (td, J=8.1, 1.2 Hz, 1H), 5.05 (dd, J=10.8, 2.1 Hz, 1H), 4.53 (d, J=10.8 Hz, 1H), 4.37 (q, J=7.2 Hz, 2H), 4.22 (d, J=8.7 Hz, 1H), 3.95 (s, 3H), 1.85 (dd, J=14.1, 8.7 Hz, 1H), 1.48 (d, J=14.1 Hz, 1H), 1.40 (t, J=7.2 Hz, 1H), 0.97 (s, 9H).

Example 6

Enantiopurity Upgrade of Compound 5

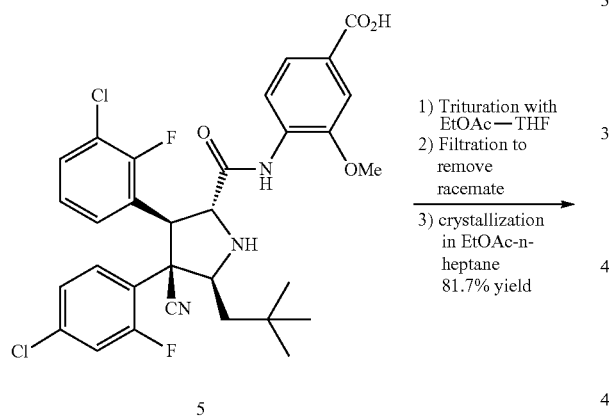

5
88% ee

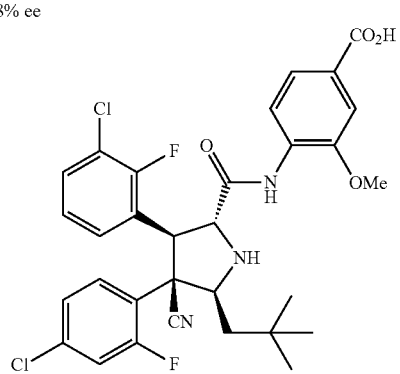

5

A 1-L, round bottomed flask equipped with a magnetic stirrer, heating mantle, condenser and nitrogen inlet/bubbler was charged with 33.4 g (54.2 mmol) of crude Compound (5), and 400 mL of tetrahydrofuran. The suspension was stirred under reflux for 1.5 h, then 100 mL of ethyl acetate was added. The mixture was stirred under reflux for additional 1.5 h, cooled to room temperature over 1.5 h, and filtered. The solid cake was washed with 60.0 mL of ethyl acetate. The filtrate and the wash were combined, and concentrated under reduced pressure to ca. 150 g, then diluted with 200 mL of ethyl acetate, and further concentrated under reduced pressure to ca. 210 g. The resulting suspension was heated to reflux, and 134 mL of heptane was added. After stirring under reflux for 1.5 h, the mixture was gradually cooled to room temperature over 3 h, stirred at room temperature overnight, and filtered. The collected solid was washed with 100 mL of ethyl acetate-heptane (1:1), 134 mL of heptane, and dried by suction and then at 60° C. under house vacuum overnight to give 27.28 g (81.7% yield) of Compound (5) as a white solid 99.96% pure, and 99.60% ee as determined by LCMS and Chiral HPLC analysis.

The invention claimed is:

1. A process for the production of compound (I)

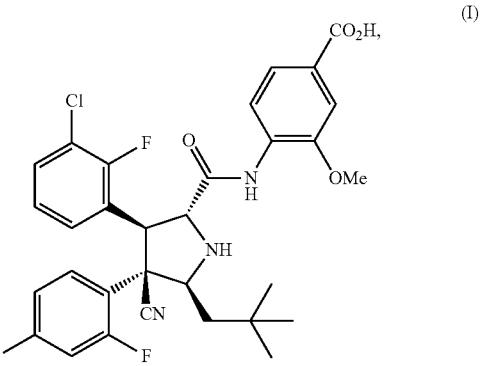

comprising the step of reacting a compound of the formula (IV)

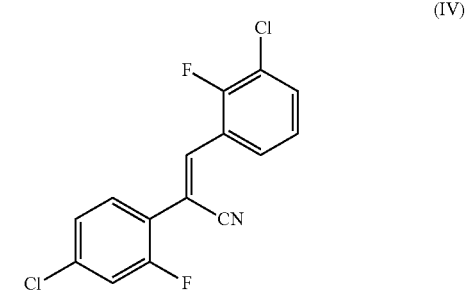 [SMILES: N#C/C(=C\c1cccc(Cl)c1F)c1ccc(Cl)cc1F]

with a compound of the formula (V)

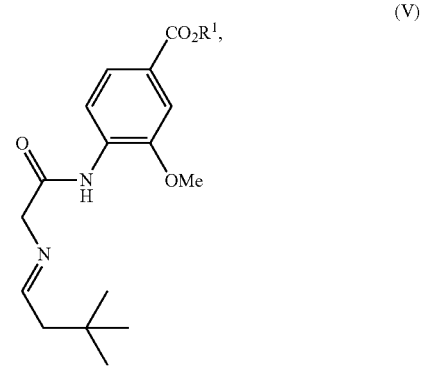

in the presence of a chiral silver- or copper catalyst and converting the compound into a compound of formula (I) wherein $R^1$ is a non-tertiary alkyl or benzyl, or other ester protecting group.

2. The process according to claim 1, comprising the steps of:

a) reacting a compound of the formula (IV)

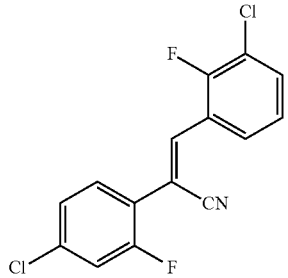

with a compound of the formula(V)

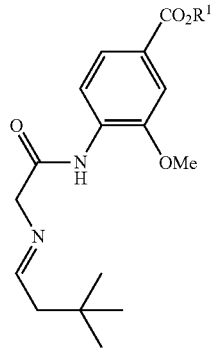

in the presence of Silver (I) together with any chiral phosphine or bidentate phosphine or other chiral ligand able to coordinate with silver metal in a non-polar or aprotic solvent in a temperature range from about −10 to about 20° C. of the selected solvent;

b) isomerising the product of (a) by reaction with a suitable base selected from a strong amine or with an insoluble base in said non-polar or aprotic solvent at a temperature range of from about 20 to 80° C.; and c) hydrolyzing the product of (h) in any suitable hydroxide in a solvent having water miscibility at a temperature between about 20 to about 80° C. to obtain a compound of formula I;

wherein $R^1$ is a non-tertiary alkyl or benzyl, or other ester protecting group.

3. The process of claim 2, wherein the insoluble base in step b) is anhydrous LiOH.

4. A process to produce a compound of the formula (I)

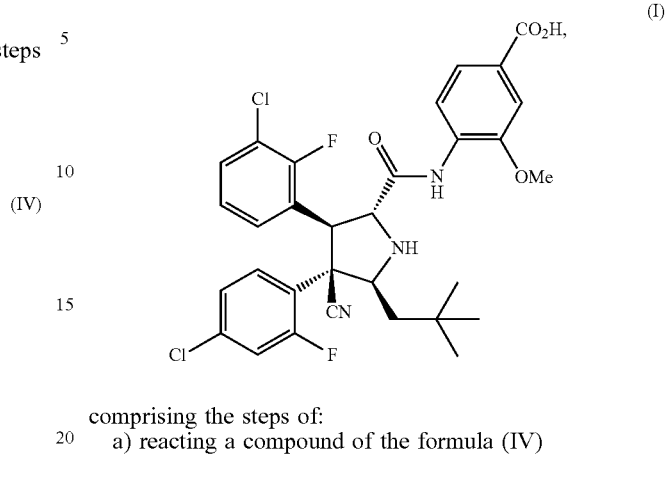

comprising the steps of:

a) reacting a compound of the formula (IV)

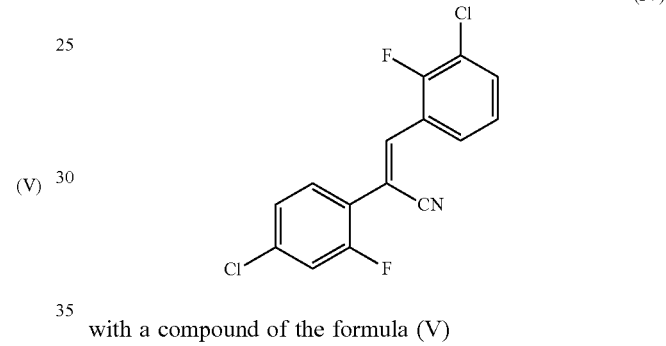

with a compound of the formula (V)

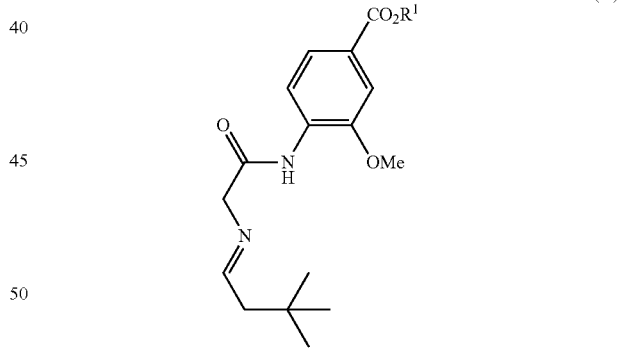

in the presence of a suitable copper source together with any chiral phosphine or bidentate phosphine or other chiral ligand able to coordinate with copper metal in a non-polar or aprotic solvent optionally together with a non-nucleophilic amine in a temperature range of about 0° C. to about 40° C.;

b) isomerising the product of (a) by reaction with a suitable base selected from a strong amine or with an insoluble base in said non-polar or aprotic solvent and at the temperature range recited in step a); and c) hydrolyzing the product of (b) in a suitable hydroxide in a solvent having water miscibility at a temperature of about 20° C. to about 80° C. to obtain a compound of formula I;

wherein $R^1$ is a non-tertiary alkyl or benzyl, or other ester protecting group.

5. The process of claim 4, wherein the copper source in a) is a chiral copper catalyst selected from a complex formed by copper (I) acetate together with a chiral phosphine or bidentate phosphine; the insoluble base in step b) is anhydrous LiOH; the suitable hydroxide in c) is aqueous sodium hydroxide (NaOH); and $R^1$ is methyl or ethyl.

6. The method according to claim 2, wherein said Silver (I) is silver acetate.

7. The method according to claim 4, wherein said suitable copper source comprises Copper (I) or Copper (II).

8. The method according to claim 5, wherein said chiral phosphine or bidentate phosphine is $PPh_3$, R- or S-BINAP or R- or S-MeOBIPHEP.

* * * * *